United States Patent [19]
Kaminsky

[11] 3,936,488
[45] Feb. 3, 1976

[54] POLYCYCLIC DIOXABORIN COMPLEXES

[75] Inventor: Daniel Kaminsky, Parsippany, N.J.

[73] Assignee: Warner-Lambert Company, Morris Plains, N.J.

[22] Filed: Oct. 17, 1974

[21] Appl. No.: 515,765

Related U.S. Application Data

[62] Division of Ser. No. 351,912, April 18, 1973, Pat. No. 3,862,144.

[52] U.S. Cl. .......................... 260/462 R; 260/345.2
[51] Int. Cl.² .................................................. C07F 5/04
[58] Field of Search .................................. 260/462 R

[56] References Cited
UNITED STATES PATENTS

| | | | |
|---|---|---|---|
| 3,177,240 | 4/1965 | Muetterties | 260/462 R |
| 3,383,401 | 5/1968 | Woods et al. | 260/462 R |
| 3,661,907 | 5/1972 | Padmanathan | 260/462 R X |

OTHER PUBLICATIONS

Smith et al. J. Org. Chem., Vol. 35, No. 10, pp. 3220-3223 (1970).

*Primary Examiner*—Helen M. S. Sneed
*Attorney, Agent, or Firm*—Albert H. Graddis; Frank S. Chow; Anne M. Kelly

[57] ABSTRACT

A process for the production of partially saturated gamma-pyrones of the general formula I:

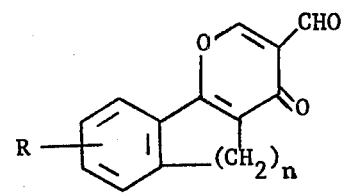

wherein R represents hydrogen, hydroxy, lower alkyl, or lower alkoxy and n represents 1 or 2, by reacting a suitably substituted tetralone (IIa) or indanone (IIb) with a boron trifluoride compound and acetic anhydride to obtain intermediate boron complexes III, which are reacted with a Vilsmeier reagent prepared from phosphorus oxychloride and dimethylformamide to obtain the partially saturated gamma-pyrones of formula I. The gamma-pyrones I have anti-allergy and anti-secretory activity.

8 Claims, 1 Drawing Figure

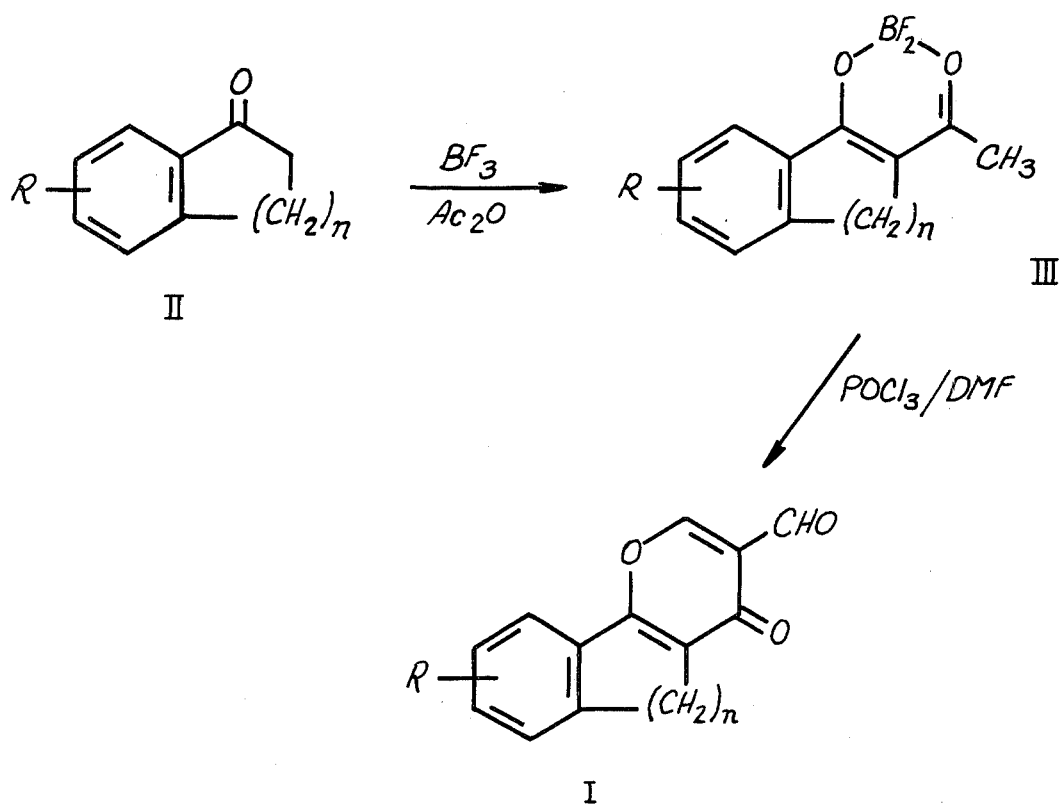

POLYCYCLIC DIOXABORIN COMPLEXES

This is a division of application Ser. No. 351,912, filed Apr. 18, 1973, now U.S. Pat. No. 3,862,144.

SUMMARY OF THE INVENTION

This invention relates to the process for preparing compounds of the formula I:

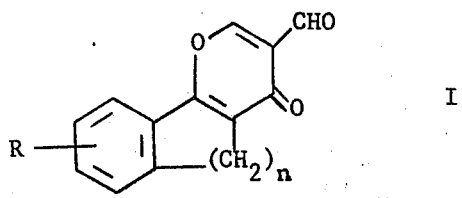

wherein R represents hydrogen, hydroxy, lower alkyl, or lower alkoxy and n represents 1 or 2, which comprises treating a compound of the formula II:

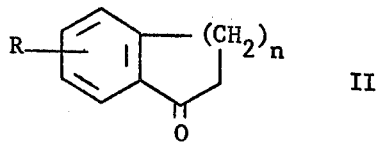

wherein R represents hydrogen, lower alkyl, lower alkoxy, or lower acyloxy, and $n$ represents 1 or 2, with an acetic anhydride and a boron trifluoride compound, to provide an intermediate of the formula III:

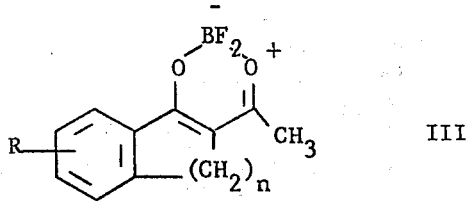

wherein R represents hydrogen, lower alkyl, lower alkoxy, or lower acyloxy and $n$ represents 1 or 2, and treating intermediate III with a Vilsmeier reagent prepared from phosphorus oxychloride and dimethylformide, followed by hydrolysis. Novel intermediates III are useful in the preparation of final compounds I which are therapeutically active as anti-allergy and anti-secretory agents.

BRIEF DESCRIPTION OF THE DRAWING

FIG. I is a schematic representation of the reaction process of the invention.

DETAILED DESCRIPTION OF THE INVENTION

In FIG. I of the drawing, the final compounds I are obtained by reacting a suitably substituted tetralone IIa ($n = 2$) or indanone IIb ($n=1$) with acetic anhydride and a boron trifluoride compound, preferably boron trifluoride etherate to obtain the novel boron complex III, which is then reacted with a Vilsmeier reagent prepared from phosphorus oxychloride (POCl$_3$) and dimethylformamide (DMF) and subjected to hydrolysis.

The substituted-tetralone (IIa) and indanone (IIb) starting materials used in the novel process of this invention are commercially available or easily prepared from available materials by known methods.

The novel boron complex intermediates III wherein $n$ represents 2 and R represents hydrogen, methyl, methoxy or acetoxy form the preferred class of novel intermediates used to prepare final compounds I having valuable therapeutic properties. In this regard, when the R substituent in intermediate III is acyloxy, such as acetoxy, hydrolysis takes place during reaction with the Vilsmeier reagent and a hydroxy substituent is formed on final compound I.

In addition, the intermediate boron complex III wherein n represents 1 and R is hydrogen can be used to prepare a similarly substituted, preferred final compound I.

Final compounds of the formula I are more fully discribed in co-pending application U.S. Ser. No. 352,135, filed Apr. 18, 1973 now abandoned in favor of Continuation-in-part application Ser. No. 480,647, filed June 19, 1974 now U.S. Pat. No. 3,887,585. The partially saturated gamma-pyrones prepared according to the process of this invention, has been found to reduce histaminic responses to antigen challenge by inhibiting antibody-antigen reactions in mammals such as rats or guinea pigs upon oral or parenteral administration. When tested in accordance with the procedure of Mota, Life Sciences, 7, 465, (1963) and Ovary, Proc. Soc. Exptl. Biol. Med., 81, 584, (1952) therapeutic compositions containing these compounds are effective at dosages of 5 mg to 50 mg/kg of body weight.

Pharmaceutical compositions containing the compounds of formula I are therefore useful in the management of allergic reactions such as bronchial asthma. To treat bronchial asthma, a dose of 5 mg to 50 mg/kg by injection or by aerosol administration is suggested. The dosage may be varied depending upon severity of the condition and the weight, age and sex of the patient being treated.

In use, the compounds of formula I may be combined with a parenterally acceptable vehicle, such as a gum tragacanth saline suspension, to provide dosage forms suitable for parenteral administration; or they may be combined with pharmaceutical diluents such as lactose, cornstarch, and the like and formulated into tablet or capsule dosage forms. In order to enhance their therapeutic spectrum, the compounds of formula I may be combined with sympathomimetic agents such as isoprenaline or combined with steroids such as cortisone and its derivatives.

The compounds of formula I also exhibit antisecretory effects and are therefore useful in relieving gastric hyperacidity. Gastric hyperacidity has generally been described as a factor which contributes to peptic ulcer. The compounds of formula I, when administered to mammals in a manner as described below, have been found to inhibit the gastric secretion of hydrochloric acid and are therefore effective in eliminating the resulting acidity in the stomach.

At a dosage of 20 mg/kg, administered intraperitoneally, the subject compositions are effective in reducing gastric acidity in the pylorus ligated rat when tested according to the procedure of H. Shay, Gastroenterology, 5, 43, (1945).

Pharmaceutical compositions containing the compounds of formula I are thus indicated in the management of gastric hyperacidity and the treatment of peptic ulcer resulting from such hyperacidity. For parenteral administration, the pharmaceutical compositions containing the compounds of formula I may be administered as aqueous suspensions for intramuscular injection. These are prepared, for example, by suspending the active ingredient in sterile water and packaging in ampules so as to provide a concentration of 1,000 mg of the active ingredient per dosage unit.

In all of the above formulas I, II, and III, the R group definitions may be more fully described as follows: the term "lower alkyl" is meant to include lower aliphatic hydrocarbons having 1 to 4 carbon atoms in the carbon chain, such as methyl, ethyl, propyl, isopropyl, butyl, or isobutyl. This definition for lower alkyl also applies to the lower alkyl portion of "lower alkoxy".

The "acyl" in the term "lower acyloxy" is meant to include lower alkyl carboxylic acids wherein the "lower alkyl" moiety has the above described meaning.

To further illustrate the practice of this invention, the following examples are included.

EXAMPLE I

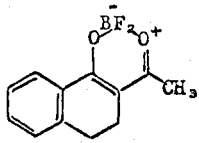

Preparation of
2,2-difluoro-5,6-dihydro-4-methylnaphtho[1,2-e]-1,3,2-dioxaborin - Method A Boron trifluoride etherate (100 g. - 0.7 mole) is added to a mixture of 73 g. (0.5 mole) α-tetralone in 204 g. (2.0 mole) of acetic anhydride. The mixture is heated on a steam bath for two hours (permitting volatiles to escape) and then gently refluxed for 1 hr. After standing overnight the mixture is triturated with cold ethyl acetate and filtered. The product is washed with ethyl ether and dried yielding 112 g. (95%) of greenish crystals; mp 156°–159°C. The analytical sample (from ethyl acetate) melted at 159°–160°C.

Anal. Calcd: $C_{12}H_{11}BF_2O_2$: C, 61.07; H, 4.70; F, 16.10. Found: C, 61.14; H, 4.72; F, 16.12.

EXAMPLE II

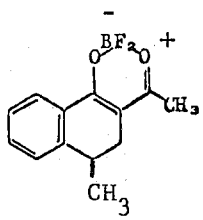

Preparation of
2,2-difluoro-5,6-dihydro-4,6-dimethylnaphtho[1,2-e]1,3,2-dioxaborin Starting with 4-methyl-α-tetralone and using method A of Example I, 2,2-difluoro-5,6-dihydro-4,6-dimethylnaphtho[1,2-e]1,3,2-dioxaborin is obtained having an mp of 120°–122°C.

Anal. Calcd: $C_{13}H_{13}BF_2O_2$: C, 62.44; H, 5.24; F, 15.20. Found: C, 62.47; H, 5.24; F, 15.21.

EXAMPLE III

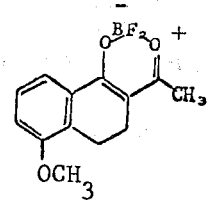

Preparation of
2,2-difluoro-5,6-dihydro-7-methoxy-4-methylnaphtho[1,2-e]1,3,2-dioxaborin Starting with 5-methoxy-α-tetralone and using method A of Example I, 2,2-difluoro-5,6-dihydro-7-methoxy-4-methylnaphtho[1,2-e]1,3,2-dioxaborin is obtained having an mp of 176°–177°C.

Anal. Calcd.: $C_{13}H_{13}BF_2O_3$: C, 58.69; H, 4.92; F, 14.28. Found: C, 58.62; H, 5.09; F, 14.24.

EXAMPLE IV

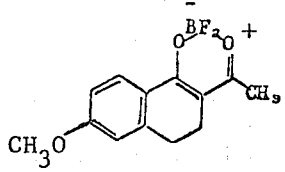

Preparation of
2,2-difluoro-5,6-dihydro-8-methoxy-4-methylnaphtho[1,2-e]1,3,2-dioxaborin Starting with 6-methoxy-α-tetralone and using method A of Example I, 2,2-difluoro-5,6-dihydro-8-methoxy-4-methylnaphtho[1,2-e]1,3,2-dioxaborin is obtained having an mp of 175°–176°C.

Anal. Calcd.: $C_{13}H_{13}BF_2O_3$: C, 58.69; H, 4.92; F, 14.28. Found: C, 58.36; H, 4.81; F, 14.23.

EXAMPLE V

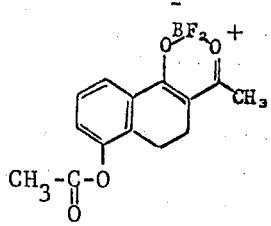

Preparation of
2,2-difluoro-5,6-dihydro-7-acetoxy-4-methylnaphtho[1,2-e]1,3,2-dioxaborin Starting with 5-acetoxy-α-tetralone and using Method A of Example I, 2,2-difluoro-5,6-dihydro-7-acetoxy-4-methylnaphtho[1,2-e]1,3,2-dioxaborin is obtained having an mp of 159°–160°C.

Anal. Calcd: $C_{14}H_{13}BF_2O_4$: C, 57.18, H, 4.46; F, 12.92. Found: C, 56.98; H, 4.41; F, 13.13.

EXAMPLE VI

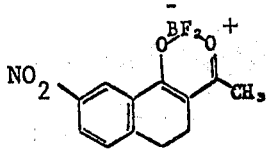

Preparation of
2,2-difluoro-5,6-dihydro-9-nitro-4-methylnaphtho[1,2-e]1,3,2-dioxaborin Starting with 7-nitro-α-tetralone and using method A of Example I, 2,2-difluoro-5,6-dihydro-9-nitro-4-methylnaphtho[1,2-e]1,3,2-dioxaborin is obtained having an mp of 176°–191°C.

Anal. Calcd: $C_{12}H_{10}BF_2NO_4$: C, 51.29; H, 3.59; F, 13.52. Found: C, 51.38; H, 3.53; F, 13.63.

EXAMPLE VII

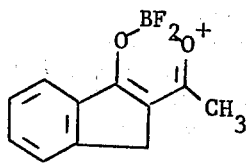

Preparation of
2,2-difluoro-4-methyl-5H-indeno[2,3-e]dioxaborin

Starting with indanone and using method A of Example I, 2,2-difluoro-4-methyl-5H-indeno[2,3-e]dioxaborin is obtained having an mp of 233°–235°C (dec.).

Anal. Calcd: $C_{11}H_9BF_2O_2$: C, 59.51; H, 4.09; F, 17.12. Found: C, 59.64; H, 4.12; F, 16.92.

EXAMPLE VIII

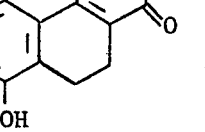

Method B – Preparation of
5,6-dihydro-4-oxo-4H-naphtho[1,2-b]pyran-3-carboxaldehyde Phosphorus oxychloride (153 g., 1.0 mole) is added dropwise to 365 g. (5.0 moles) of dimethyl formamide with cooling in order to maintain temperature below 10°C. The mixture is stirred for an additional 10-15 minutes and 118 g. (0.5 mole) of 2,2-difluoro-5,6-dihydro-4-methylnaphtho[1,2-e]1,3,2-dioxaborin is added. The mixture is then heated for two hours on a steam bath and poured cautiously into 4 liters of cold water. After standing for several hours with occasional stirring, the mixture is filtered to yield, after drying, 202 g. (89.5%) dark brown product; mp 153°–156°C. The analytical sample (from acetonitrile) melted at 154°–156°C.

Anal. Calcd for $C_{14}H_{10}O_3$: C, 74.33; H, 4.46; O, 21.22. Found: C, 74.33; H, 4.41; O, 21.05.

EXAMPLE IX

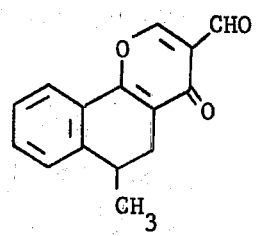

Preparation of
5,6-dihydro-6-methyl-4-oxo-4H-naphtho[1,2-b]pyran-3-carboxaldehyde Starting with 2,2-difluoro-5,6-dihydro-4,6-dimethylnaphtho[1,2-e]1,3,2-dioxaborin and using method B of Example VIII, 5,6-dihydro-6-methyl-4-oxo-4H-naphtho[1,2-b]pyran-3-carboxaldehyde is obtained having an mp of 146°–148°C.

Anal. Calcd: $C_{15}H_{12}O_3$: C, 74.99; H, 5.03; O, 19.98. Found: C, 74.90; H, 5.07; O, 19.83.

EXAMPLE X

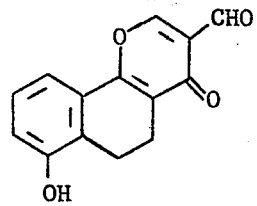

Preparation of
5,6-dihydro-7-hydroxy-4-oxo-4H-naphtho[1,2-b]pyran-3-carboxaldehyde Starting with 2,2-difluoro-5,6-dihydro-7-acetoxy-4-methylnaphtho[1,2-e]1,3,2-dioxaborin and using method B of Example VIII, 5,6-dihydro-7-hydroxy-4-oxo-4H-naphtho[1,2-b]pyran-3-carboxaldehyde is obtained having an mp of 255°–256°C. (dec.)

Anal. Calcd: $C_{14}H_{10}O_4$: C, 69.42; H, 4.16; O, 26.42. Found: C, 69.58; H, 5.20; O, 26.68.

EXAMPLE XI

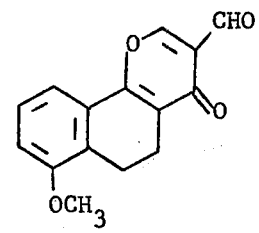

Preparation of
5,6-dihydro-7-methoxy-4-oxo-4H-naphtho[1,2-b]pyran-3-carboxaldehyde Starting with 2,2-difluoro-5,6-dihydro-7-methoxy-4-methylnaphtho[1,2-e]1,3,2-dioxaborin and using method B of Example VIII, 5,6-dihydro-7-methoxy-4-oxo-4H-naphtho[1,2-b]-pyran-3-carboxaldehyde is obtained having an mp of 201°–202°C.

Anal. Calcd: $C_{15}H_{12}O_4$: C, 70.30; H, 4.72. Found: C, 70.23; H, 4.73.

EXAMPLE XII

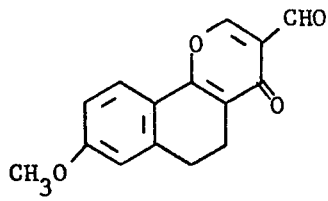

Preparation of
5,6-dihydro-8-methoxy-4-oxo-4H-naphtho[1,2-b]pyran-3-carboxaldehyde Starting with 2,2-difluoro-5,6-dihydro-8-methoxy-4-methylnaphtho[1,2-e]1,3,2-dioxaborin and using method B of Example VIII, 5,6-dihydro-8-methoxy-4-oxo-4H-naphtho[1,2-b]pyran-3-carboxaldehyde is obtained having an mp of 186°–187°C. (dec.)

Anal. Calcd: $C_{15}H_{12}O_4$: C, 70.30; H, 4.72; O, 24.98. Found: C, 70.11; H, 4.77; O, 24.78.

I claim:

1. Compounds of the formula III:

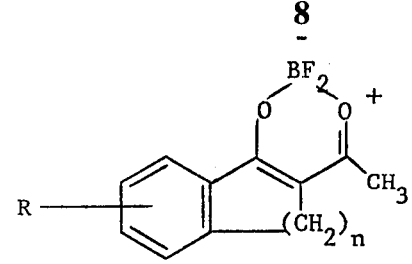

wherein R is hydrogen, lower alkyl, or lower acyloxy and $n$ represents 1 or 2.

2. A compound according to claim 1 wherein R is hydrogen, methyl, or acetoxy and $n$ is 2.

3. A compound according to claim 1 wherein R is hydrogen and $n$ is 1.

4. A compound according to claim 2 which is 2,2-difluoro-5,6-dihydro-4-methylnaphtho[1,2-e]-1,3,2-dioxaborin.

5. A compound according to claim 2 which is 2,2-difluoro-5,6-dihydro-4,6-dimethylnaptho[1,2-e]1,3,2-dioxaborin.

6. A compound according to claim 2 which is 2,2-difluoro-5,6-dihydro-7-acetoxy-4-methylnaphtho[1,2-e]-1,3,2-dioxaborin.

7. A compound according to claim 5 which is 2,2-difluoro-4-methyl-5H-indeno[2,3-e]dioxaborin.

8. 2,2-Difluoro-5,6-dihydro-9-nitro-4-methylnaphtho[1,2-e]-1,3,2-dioxaborin.

* * * * *